US008048443B2

(12) United States Patent
Benedict et al.

(10) Patent No.: US 8,048,443 B2
(45) Date of Patent: Nov. 1, 2011

(54) PLIABLE MEDICAL DEVICE AND METHOD OF USE

(75) Inventors: James John Benedict, Arvada, CO (US); Greg Allen Brewster, Arvada, CO (US); Donald Barclay Freeman, Wheat Ridge, CO (US)

(73) Assignee: Cerapedics, Inc., Lakewood, CO (US)

( * ) Notice: Subject to any disclaimer, the term of this patent is extended or adjusted under 35 U.S.C. 154(b) by 1008 days.

(21) Appl. No.: 11/305,715

(22) Filed: Dec. 16, 2005

(65) Prior Publication Data

US 2007/0141103 A1 Jun. 21, 2007

(51) Int. Cl.
*A61F 2/00* (2006.01)
*A61K 38/18* (2006.01)
(52) U.S. Cl. .......................... 424/426; 514/7.6
(58) Field of Classification Search .................. None
See application file for complete search history.

(56) References Cited

U.S. PATENT DOCUMENTS

| | | | |
|---|---|---|---|
| 3,728,446 A | 4/1973 | Roberts et al. | |
| 4,530,942 A * | 7/1985 | Dhabhar et al. | 523/118 |
| 5,207,983 A * | 5/1993 | Liebert et al. | 422/25 |
| 5,354,736 A | 10/1994 | Bhatnagar | |
| 5,635,482 A | 6/1997 | Bhatnagar | |
| 5,674,848 A | 10/1997 | Bhatnagar | |
| 5,681,873 A | 10/1997 | Norton et al. | |
| 5,910,315 A | 6/1999 | Stevenson et al. | |
| 5,922,025 A | 7/1999 | Hubbard | |
| 5,958,428 A | 9/1999 | Bhatnagar | |
| 6,030,635 A | 2/2000 | Gertzman et al. | |
| 6,203,573 B1 | 3/2001 | Walter et al. | |
| 6,214,368 B1 | 4/2001 | Lee et al. | |
| 6,268,348 B1 | 7/2001 | Bhatnagar | |
| 6,287,341 B1 | 9/2001 | Lee et al. | |
| 6,326,018 B1 | 12/2001 | Gertzman et al. | |
| 6,340,477 B1 | 1/2002 | Anderson | |
| 6,432,437 B1 | 8/2002 | Hubbard | |
| 6,485,751 B1 | 11/2002 | Wang | |
| 6,537,574 B1 | 3/2003 | Hubbard | |
| 6,537,589 B1 | 3/2003 | Chae et al. | |
| 6,630,153 B2 | 10/2003 | Long et al. | |
| 6,692,760 B2 | 2/2004 | Miyamoto et al. | |
| RE38,522 E | 5/2004 | Gertzman et al. | |
| 6,818,620 B2 | 11/2004 | Bhatnagar | |
| 6,974,862 B2 | 12/2005 | Ringeisen et al. | |
| 7,060,287 B1 | 6/2006 | Hubbard et al. | |
| 2002/0018796 A1 | 2/2002 | Wironen | |
| 2002/0071827 A1 | 6/2002 | Petersen et al. | |
| 2002/0192263 A1 | 12/2002 | Merboth et al. | |
| 2003/0009235 A1* | 1/2003 | Manrique et al. | 623/23.63 |
| 2003/0077825 A1 | 4/2003 | Bhatnagar et al. | |
| 2003/0143283 A1 | 7/2003 | Tofe | |
| 2004/0062816 A1 | 4/2004 | Atkinson et al. | |
| 2004/0091462 A1 | 5/2004 | Lin et al. | |
| 2004/0185021 A1 | 9/2004 | Hubbard | |
| 2004/0197373 A1 | 10/2004 | Gertzman et al. | |
| 2005/0100533 A1 | 5/2005 | Bhatnagar et al. | |
| 2005/0118230 A1* | 6/2005 | Hill et al. | 424/426 |
| 2005/0164944 A1 | 7/2005 | Bhatnagar | |
| 2005/0177238 A1 | 8/2005 | Khandkar et al. | |
| 2006/0173551 A1 | 8/2006 | Hubbard et al. | |
| 2006/0246397 A1 | 11/2006 | Wolf | |
| 2007/0141103 A1 | 6/2007 | Benedict et al. | |

FOREIGN PATENT DOCUMENTS

WO   WO 86/01113   2/1986
WO   WO 03/063686  8/2003

OTHER PUBLICATIONS

Nguyen, Hieu et. al., Enhanced cell attachment and osteoblastic activity by P-15 peptide-coated matrix in hydrogels, Biochemical and Biophysical Research Communicatins 311 (2003) 179-186.*
Davies, Jeffrey P. et. al., Optimization and Comparison of Three Vacuum Mixing Systems for Porosity Reduction of Simplex P Cement, Clinical Orthopedics and Related Research, No. 254, May 1990, pp. 261-269.*
Schrier, Jay A. et al., Effect of Freeze-Dried CMC/PLGA Microsphere Matrix of rhBMP-2 on Bone Healing, AAPS PharmscTech, 2 (3) article 18, 2001, pp. 1-8.*
Nguyen et al., Enhanced Cell Attachment and Osteoblastic Activity by P-15 Peptide-Coated Matrix in Hydrogels, Biochem Biophys Res Commun., Nov. 7, 2003, pp. 179-186, vol. 1, No. 311, Publisher: Department of Bioengineering and the Center for Tissue Engineering, Published in: USA.
Thorwarth et al., Bioactivation of an Anorganic Bone Matrix by P-15 Peptide for the Promotion of Early Bone Formation, Biomaterials, Apr. 18, 2005, p. 28 volume Oct. 2005, No. 26, Publisher: University of Jena, Published in: Germany.
Gelbart et al., Maxillary Sinus Augmentation Using a Peptide-Modified Graft Material in Three Mixtures, Implant Dent., Jun. 14, 2005, pp. 185-193, vol. 2, No. 14, Published in: USA.
Healos Bone Graft Replacement, http://www.medcompare.com/details/20376/Healos-Bone-Graft-Replacement.html, Sep. 13, 2005, Publisher: Medcompare, Published in: USA.
Vitoss Synthetic Cancellous Bone, Sep. 13, 2005, Publisher: http://www.orthovita.com/products/vitoss/index.html, Published in: USA.

(Continued)

*Primary Examiner* — Kevin Hill
*Assistant Examiner* — Lyndsey Beckhardt
(74) *Attorney, Agent, or Firm* — Clark & Elbing LLP

(57) ABSTRACT

A firm but pliable medical device for use as a bone graft substitute or bone graft extender retains its shape without the requirement of a containment device, such as a syringe. Because the device is solid, it is easy to locate or position in-vivo and, in the moist environment of the body, it will hold its shape well, for an extended time. Because the lyophilized pliable medical device is porous, it adsorbs blood and other beneficial cells containing body fluids, such as bone marrow, contributing to its superior bone repair efficacy in comparison to an analogous putty that has not been lyophilized. In addition these lyophilized pliable medical devices are easier to terminally steam sterilize than the analogous putty because there is no moisture present to boil and "blow-out" of the containment device (syringe). The glycerin that is present in the formulation lends pliability but has a low vapor pressure.

17 Claims, 3 Drawing Sheets

OTHER PUBLICATIONS

Atkinson et al., the Academy of Osseointergration 19$^{th}$ Annual Meeting, Mar. 2004, San Francisco, CA. (abstract of poster).

Patel e al., "Autograft Versus P-15 in an Uninstrumented Sheep Lumbar Spine Fusion Model," The Spine Journal 7:8S (2007).

International Report on Patentability for PCT/US2006/047970, dated Oct. 7, 2008.

Gelbart et al., "Maxillary Sinus Augmentation Using a Peptide-Modified Graft Material in Three Mixtures: A Prospective Human Case Series of Histologic and Histomorphometric Results," *Implant Dent.* 14:185-193, 2005.

Thorwarth et al., "Bioactivation of an Anorganic Bone Matrix by P-15 Peptide for the Promotion of Early Bone Formation," *Biomaterials* 26:5648-5657, 2005.

International Search Report for International Application No. PCT/US2006/047970, completed Oct. 7, 2008.

\* cited by examiner

PLIABLE MEDICAL DEVICE AND METHOD OF USE

FIELD OF THE INVENTION

This invention relates to the field of surgical repair of skeletal elements. More particularly, the invention is a method and composition for use as a bone graft substitute or bone graft extender for filling or otherwise repairing bone damage and promoting bone formation in mammals using a composition that is a firm but pliable medical device that will retain its shape without the requirement of a containment device, such as a syringe.

BACKGROUND OF THE INVENTION

Physicians are sometimes called upon to repair bone that has been damaged by disease, trauma, osseous surgery or other causes, or to cause bone material to grow where there has been no bone before, such as during a spine fusion procedure. As an outcome of that procedure, it is desirable for two or more vertebral bodies to be maintained in a specific orientation. This can be accomplished by growing a column or bridge of rigid bone between the vertebral bodies. This maintains them in a fixed position relative to each other. The repair of long bone fractures can often be accomplished merely by relocating disrupted bone elements into natural proximity and fixing them in place until they can heal together. This is the approach taken in repairing ordinary limb fractures, for example. The fractured bone is re-set, then immobilized for a period of weeks in a rigid or semi-rigid cast or splint as the fractured elements heal.

Sometimes, however, this approach is insufficient because the patient has lost some of the bone. This can happen in certain kinds of trauma where the bone is so badly shattered that it cannot feasibly be pieced together. More often, it happens as a result of disease that destroys bone mass or as the result of osseous surgery in which destruction of bone mass is unavoidable. In these cases, there is no "piece" of the patient's bone to re-set into proper position for healing. Instead, there is a void or defect that must somehow be filled, or a gap between two bone structures that needs to be filled with new bone. The filling of this defect or gap requires a material that is not only biocompatible but preferably will accept or even promote in-growing natural bone as the site heals. In such a manner, the material ideally will eventually become resorbed as new in-growing natural bone takes its place as part of the skeletal structure. Completely resorbed material eliminates the possibility for a stress riser that can occur when foreign matter remains in the skeleton, potentially giving rise to a fracture in the future.

Numerous bone replacement materials have been employed by physicians with varying degrees of success. One approach is to use bone material recovered from the patient himself, or so-called autologous bone. This approach is advantageous in that it avoids biocompatibility and bio-rejection problems. However, such an approach necessarily involves two surgical procedures, two surgical sites, and two healing processes-one for the original injury and a second for the site of the donated bone material. This means greater cost, and increased risk of infection and morbidity for a patient that is already seriously ill or injured. Also, this approach can require a great deal of time and surgical skill as the surgeon removes the donated material from the donation site, shapes and fits it to the primary site, and then repairs both sites. Finally, there is quite obviously a limit to the amount of bone in the patient's body available to be sacrificed as donor material.

Another approach uses human bone but not harvested from the patient. This is called allograft bone. Allograft bone is typically harvested from cadavers. It contains endogenous bone morphogenic proteins ("BMP") and is available both in structurally intact and demineralized forms. Such material can become integrally incorporated into the patient's own skeletal system.

Demineralized allograft is routinely offered by commercial medical suppliers in dry granulated or powdered form of varying fineness. These dry granules or powder generally lack sufficient cohesiveness and adhesion for filling an osseous defect. Therefore, they are mixed with an appropriate carrier. The carrier in the past has sometimes been the patient's own blood or bone marrow. Such a carrier is of course plentiful at the surgical site, is biocompatible with the patient, and contains biological agents that promote new growth in the allograft bone elements suspended in it. On the other hand, using the patient's own blood necessitates a mixing step which might not be controlled precisely in the operating room to achieve the desired consistency. In addition, blood is not of the ideal consistency or viscosity for such an application.

Glycerol and other biocompatible materials have been used as alternate carriers in combination with demineralized allograft bone. Glycerol is suitable in consistency and viscosity for this application, but suffers from certain functional drawbacks. Because glycerol is water soluble, it could allow early dispersement of the suspended bone after being placed in the bone defect at the injury site.

Purified forms of human or animal derived collagen have been described previously for use in bone graft substitutes. When used by itself, in lyophilized form, collagen is not entirely suitable for use as a bone graft substitute. It resorbs too quickly to be an effective scaffold for bone accretion. In order for bone formation to occur, osteogenic cells (cells capable of producing bone) must attach to the osteoconductive substrate and begin the process of bone formation. The substrate must remain present long enough to allow bone formation to progress to the point of being self sustaining. Collagen can be chemically modified to make it less bioresorbable. Chemical cross linking agents such as formaldehyde and glutaraldehyde have been described. Unfortunately, low residual levels of these agents are cytotoxic and can affect bone formation in a negative manner.

Lyophilized collagen devices also compress, under soft tissue forces, not maintaining an adequate space for bone ingrowth to occur. In such circumstances, collagen can be used in combination with alloplast materials for maintaining an adequate "healing volume." Even in these instances though, collagen still suffers the disadvantage of being a possible sensitizing agent in patients at risk for having an allergic response to collagen. In the case of bovine or other animal collagen, there is also a concern about the transmission of animal diseases, such as Bovine Spongiform Encephalopathy (BSE, or Mad Cow Disease) to the patient.

As a substitute for glycerol, high-molecular weight hydrogels, such as sodium hyaluronate, have been used to form a malleable bone putty which includes allograft bone powder suspended therein. Hyaluronon is a polysaccharide that occurs naturally in the body in the form of hyaluronic acid or in the salt form such as sodium hyaluronate. It is highly hydrophilic, viscous, and extremely lubricous. High-molecular weight hydrogels will allow suspension of very small particle sizes of allograft material.

However, even hydrogels may tend to disperse from the bone defect site. In addition, hydrogels are not conducive to retaining the body's own fluids or bone marrow aspirate which may be delivered to the defect site. There is therefore a need in the art for an improved bone graft substitute that overcomes these and other deficiencies.

DETAILED DESCRIPTION OF THE INVENTION

Figure 1:
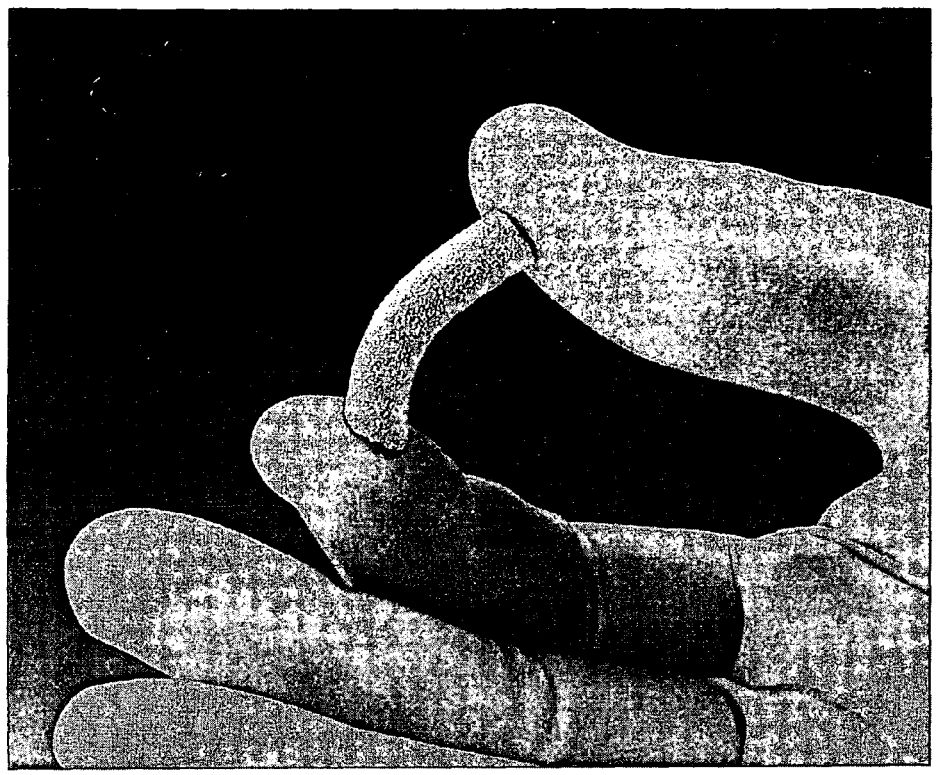
FIG. 1 shows a picture of a cylinder shaped embodiment of the pliable medical device of the present invention and its flexibility.

The nature of the present invention begins with the preparation of a hydrogel material. The following description is by way of example, and specific amounts of material listed may be varied substantially to achieve the same or similar results. Thus, the specific amounts shown below are by way of example only and are not intended to be limiting to the scope of the invention.

A mixing operation is performed in a stainless steel, one quart, Ross double planetary mixing unit fitted with a closure allowing for operation under partial vacuum. First, 31.5 grams of sodium carboxymethylcellulose (NaCMC) is completely dispersed in 145.3 grams of glycerin (USP). The dispersion is added in approximately equal amounts to each of three 60 ml disposable plastic Luer-lock fitted syringes. Alternatives to glycerin are possible, such as polyethylene glycols, N-methyl pyrrolidone, and triacetin.

With the mixing unit under partial vacuum (15 inches of mercury (Hg)) one of the NaCMC dispersion containing syringes is connected to the mixing unit via a Luer-lock fitted entry port and the contents of the syringe are added to the mixing unit. While mixing at a moderate speed (100 rpm) about 30% of a total of 823.2 grams of sterile water for injection (WFI) is added to the mixing unit. Next, the contents of a second NaCMC dispersion containing syringe is added to the mixing unit along with an additional 30% of the total WFI. Finally, contents from the third NaCMC dispersion containing syringe and all but about fifty ml of the remaining WFI is added to the mixing unit. The remainder of the WFI is used to rinse the syringe entry port. The vacuum in the mixing unit is adjusted to greater than twenty inches of Hg and the contents mixed at medium speed (150 rpm) for about thirty-five minutes. Then, the vacuum is broken and mixing discontinued. The resulting hydrogel material from the mixing unit is transferred to a closed storage container. The hydrogel material is allowed to hydrate at room temperature, about 25° C. for at least six hours. The process may be speeded up by placing the closed storage container in an environment with an elevated temperature, such as 40° C.

Next, about 240 grams of the hydrated hydrogel material is transferred to the mixing unit along with about 130 grams of anorganic bone mineral matrix (ABM), a calcium phosphate ceramic, which may be coated with a biologically active peptide. Several different biologically active peptides may be used. For example, P-15 is a peptide fragment taken from Type I collagen and acts as a cell binding agent. Chrysalin is a peptide fragment taken from the biomolecule thrombin. Chrysalin is reported to have effects on blood vessel formation. Cytomodulin is a bioactive 7 amino acid synthetic protein patterned after a peptide sequence found in the biomolecule TGF-beta. Cytomodulin is further described in U.S. Pat. No. 5,661,127. The alpha1(I)-CB3 fragment of type I collagen contains the reportedly biologically active fragment DGEA [J. Biol. Chem, 266(12) p-7363 (1991)] that bind the alpha2/beta1 integrin. Type I collagen also contains the well know RGD peptide sequence that acts as a fibronectin receptor. There are well known peptide fragments of the parathyroid hormone, e.g., the 1-34 PTH fragment, that have biological activity on the skeleton. Other examples of biologically active synthetic peptide fragments based on sequences from the biomolecules Angiotensin I and II are described in U.S. Pat. No. 6,916,783. These biologically active peptides may also be used in these pliable medical devices.

ABM is the "osteoconductive component" of the pliable medical device. An osteoconductive material is one that promotes bone deposition, provided that fully differentiated and competent osteogenic cells are available at the site of implantation. In addition to anorganic bone mineral matrix (ABM), the osteoconductive component may also be a synthetic alloplast matrix or some other type of xenograft or allograft mineralized matrix that might not fit the definition of "anorganic." The alloplast could be a calcium phosphate material or it could be one of several other inorganic materials that have been used previously in bone graft substitute formulations, e.g., calcium carbonates, calcium sulphates, calcium silicates, or mixtures thereof that could function as biocompatible, osteoconductive matrices. The anorganic bone mineral matrix, synthetic alloplast matrix, and xenograft or allograft mineralized matrix are collectively referred to as the osteoconductive component.

The P-15 material mentioned previously is structurally identical to a fifteen amino acid sequence that is found in natural Type I collagen, but is made synthetically. The P-15 used is not osteoinductive (having the ability to induce de novo differentiation of competent osteogenic cells from nonosteogenic and uncommitted cells). The P-15 will not take non-bone cells and make bone cells out of them, but instead, P-15 is able to recruit cells that are already destined to become bone cells (osteogenic) and cause them to lay down on the surface of the matrix and start making bone. This is advantageous in the event that the pliable medical device migrates away from the osteogenic site, i.e., a site predisposed to growing bone cells. In such an event, no bone cells will grow at the site of migration, whereas, an osteoinductive material, typical of the prior art products, could cause ectopic bone to grow wherever the material happened to migrate, which could be very detrimental and problematic for the patient. The pliable medical device needs to be in physical contact with an osteogenic site in order for bone to grow. Thus, in a spine fusion application, a cylinder of the pliable medical device positioned at each end, adjacent to different vertebra, will allow bone to grow from each end, and meet in the middle, forming a new bone structure that was not there before.

The P-15 coated ABM particles have a mean particle diameter of 300 microns, and nearly all will fall within a range between 250 microns to 425 microns. However, a particle size range between 50 microns to 2000 microns may also be used. The two materials, ABM and the hydrated hydrogel material, are mixed at low speed (approximately fifty rpm) for about two minutes. Next, a second 130 gram amount of ABM/P-15 particles are added and mixed for an additional seventeen minutes. A vacuum of at least twenty inches of Hg is drawn on the mixing unit and mixed for an additional five minutes. The resulting ABM/P-15/CMC hydrogel material, hereinafter referred to as "putty", is transferred from the mixing unit and may be stored, or processed further according to the following steps.

Though the putty can be used by a physician in this form to treat bone damage, it may be further processed by a lyophilization step into several different shapes. The following examples are simply illustrative and not intended to be limiting to only the shapes described. In addition to the cylinder, cube, and sheet shapes described below, any other shapes for a particular purpose could be made, such as star shaped, toroid shaped, pyramid shaped, sphere shaped, and any number of irregularly shaped embodiments.

Example 1

Preparation of Lyophilized Cylinders

An extrusion device is fitted with a 6.5 mm diameter orifice and filled with the putty prepared as described above. Cylinders, fifty mm in length, are extruded from the device onto a chilled (−30° C.) metal plate, or any other appropriate chilled surface. The cylinders are further cooled to −55° C. on the shelves of a lyophilization vessel. Lyophilization is a means of water removal, achieved by freezing a wet substance and causing the ice to sublime directly to vapor by exposing it to a surrounding low pressure. A vacuum of 200 mTorr is applied to the frozen cylinders and maintained for eighteen hours. During that time the lyophilization chamber is allowed to warm to room temperature, approximately 25° C., or heated somewhat to speed up the sublimation process. These conditions are sufficient to reduce the water content of the cylinders to about 3%. The resulting lyophilized cylinders are dry in appearance, flexible and able to absorb blood and serous fluids. Please see FIGS. 1-3.

Lyophilization has many advantages over simply air drying or vacuum drying the putty. When the putty is allowed to air dry or vacuum dry without freezing, the hydrogel forms a skin around the ABM particles that is occlusive and prevents cells from getting to the particles. Freezing the material first, and then evaporating the water leaves many holes where the ice crystals sublime giving rise to a very porous structure. The porous structure allows cells, blood, and bone marrow easy access through the holes to the particles. With air drying and vacuum drying without freezing, the hydogel structure continues to collapse as the water evaporates, thus preventing the creation of a porous structure. Sublimation, rather than evaporation, is the key to creating the porous structure desired.

Next, the lyophilized cylinders are placed into sealed but breathable microbial barrier pouches and sterilized in a steam autoclave. The pouches may be made of paper or more typically Tyvec® from DuPont. The sterilization cycle includes a twenty minute temperature ramp-up to 121° C., temperature maintenance at 121° C. for thirty minutes, followed by a one hour cool down period to room temperature, approximately 25° C. The lyophilized cylinders are substantially unchanged in their physical handling properties following this sterilization procedure.

Figure 2:
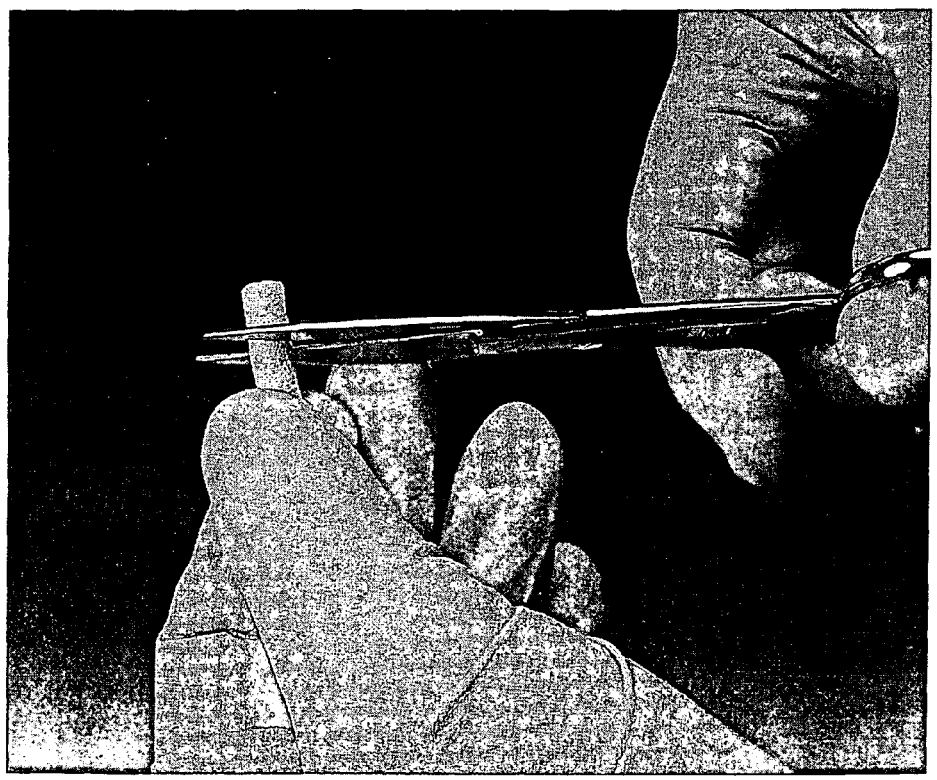
FIG. 2 shows a picture of a cylinder shaped embodiment of the pliable medical device of the present invention being cut with scissors.
Figure 3:
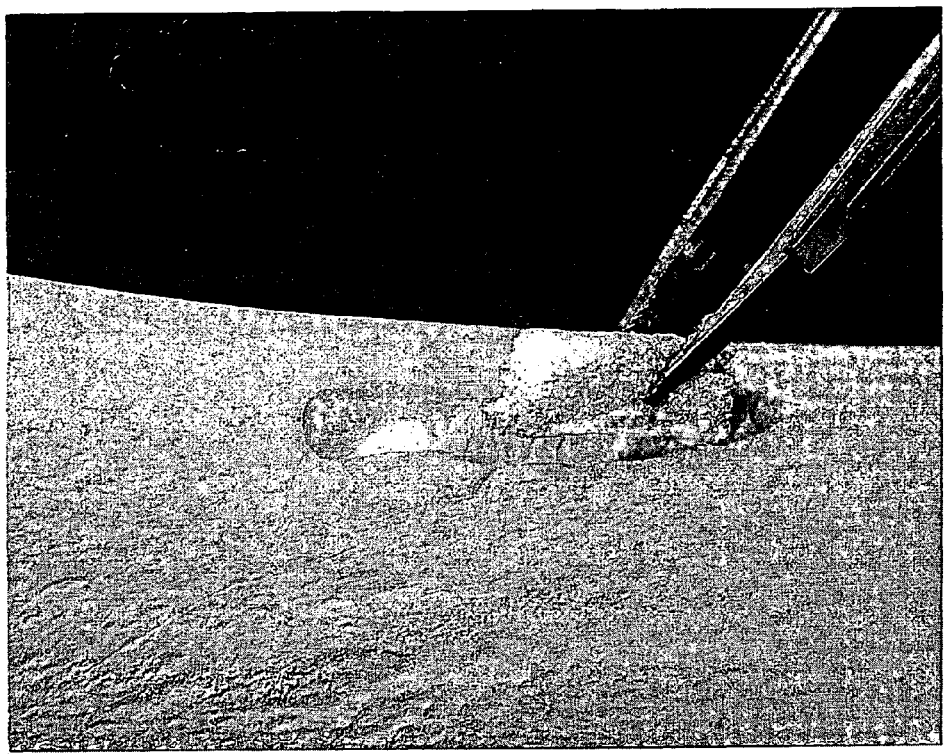
FIG. 3 shows a picture of a cylinder shaped embodiment of the pliable medical device of the present invention being placed into a bone defect.
Figure 5:
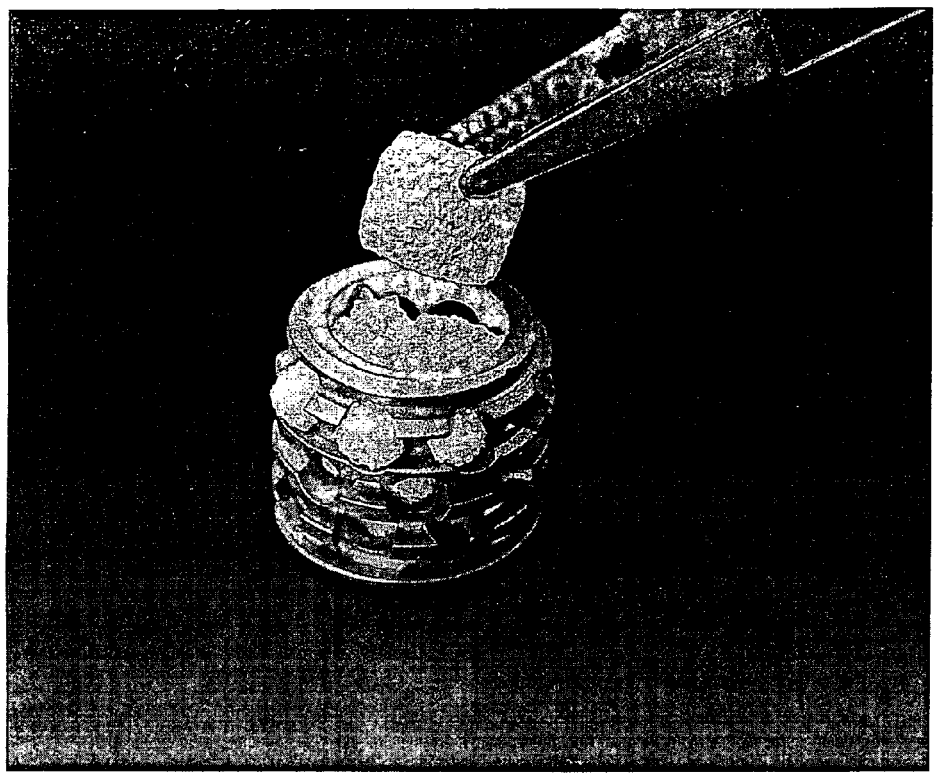
FIG. 5 shows a picture of a cube shaped embodiment of the pliable medical device of the present invention being placed into a metal spine fusion cage.

Because the lyophilized cylinders are easily cut into smaller pieces as shown in FIG. 2, it is easy to load those pieces directly into a osteogenic site, such as the bone defect shown in FIG. 3, or into metal spine fusion cages, such as the BAK-C cage shown in FIG. 5. This loading can be done before the cage is placed into the prepared inter-body location during an anterior cervical spine discectomy and vertebral body fusion.

Example 2

Preparation of Lyophilized Sheets

Figure 4:
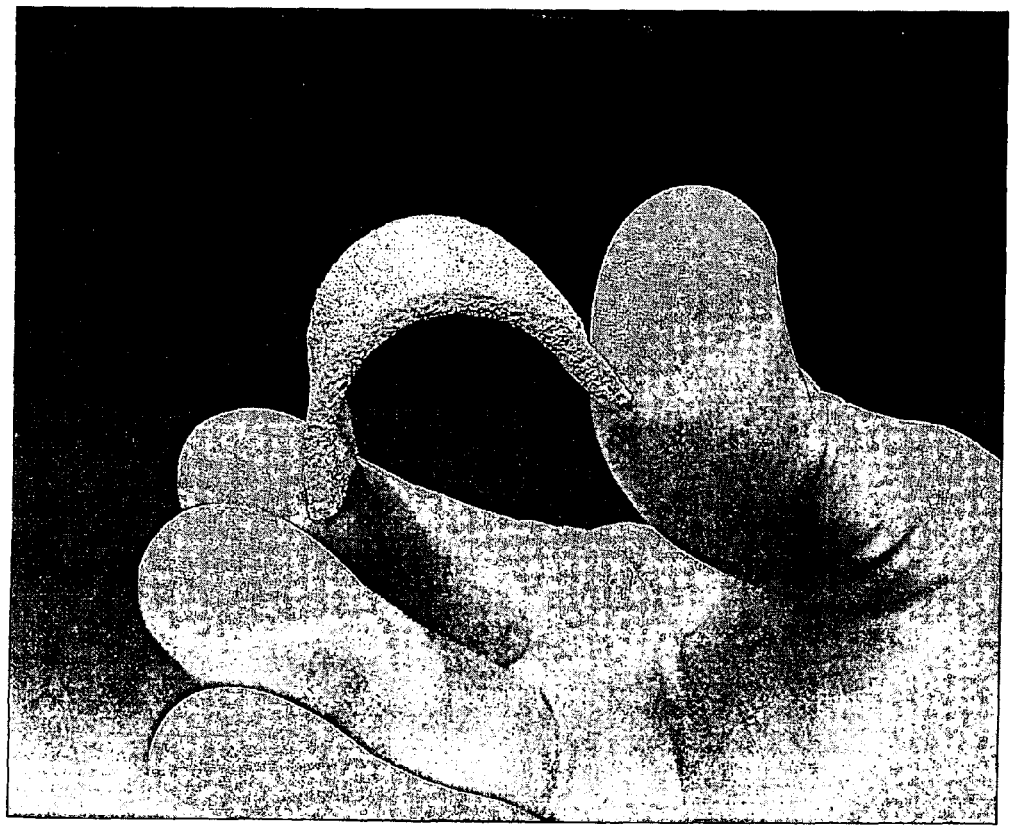
FIG. 4 shows a picture of a sheet embodiment of the pliable medical device of the present invention and its flexibility.

The putty prepared as described above is loaded by injection into a Delrin mold containing a channel, twenty-four mm wide by four mm deep by 150 mm in length. The sheet-like mold is fitted with a releasable top plate that is typically bolted to the bottom plate. The loaded sheet-like mold is placed into a freezing unit and the sheet-like mold and putty are cooled to −55° C. After reaching this desired temperature, the top plate of the sheet-like mold is loosened to allow water to sublime away, and the sheet-like mold, still cold, is placed into a lyophilization chamber at 135 mTorr. During the sublimation process the lyophilization chamber is allowed to gradually warm to room temperature, approximately 25° C., or heated somewhat to speed up the sublimation process. The resulting dry flexible lyophilized sheet is easily removed from the mold and cut with standard scissors (FIG. 4). The lyophilized sheet is compliant for fitting onto an irregular surface. When dampened, the sheet maintains its proximity to the applied surface very well. The lyophilized sheet could also be sterilized in a steam autoclave as described above, prior to use.

High energy tibial fractures (auto accidents) are prone to becoming non-unions. These non-unions are often repaired by debrieding the soft tissue from the non-union area and loading the open space between the fracture ends with autograft bone. To better localize the autograft bone, a lyophilized sheet would be wrapped around the tibia enclosing the non-union in a "repair burrito." The musculature and other soft tissues would then envelope the repair site.

Example 3

Preparation of Lyophilized Cubes

The putty prepared as described above is pressed into a Delrin mold, using a stainless steel laboratory spatula, or any other suitable utensil, or by hand, to create cubes, one centimeter on edge. The mold and putty is frozen on a dry ice slab, or any suitably chilled surface or freezer shelf or with liquid nitrogen, and placed, still frozen, into a lyophilization flask. The putty is then subjected to a vacuum of 125 mTorr for forty-eight hours while warming the lyophilization chamber to room temperature, approximately 25° C. The lyophilized cubes can be sterilized in a steam autoclave, as described above, prior to use. The lyophilized cubes are dry in appearance but flexible and readily soak up blood and mix easily with bone marrow aspirate. The lyophilized cubes could be mixed with autograft bone harvested by conventional techniques from areas such as the iliac crest and serve to expand the useful volume of bone graft material available to the orthopedic surgeon.

When cancellous autograft bone is harvested from the iliac crest, a cortical bone window is cut from the top of the ilium and cancellous bone is harvested from the space between the inner and outer cortical bone tables. Lyophilized cubes (or cylinders) are easily placed into the void created by the removal of the cancellous bone graft (FIG. 3). The lyophilized cubes would facilitate the re-growth of host bone.

Figure 6:
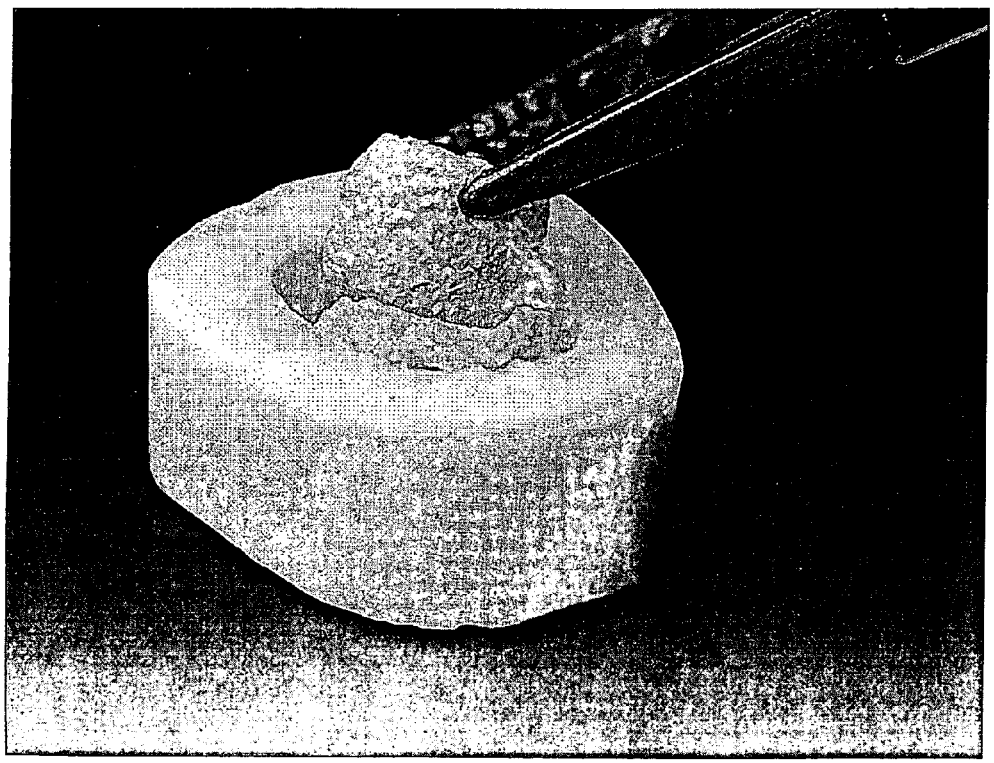
FIG. 6 shows a picture of a cube shaped embodiment of the pliable medical device of the present invention being placed into a hollow central portion of a fibular ring allograft device.

Lyophilized cubes or short lyophilized cylinders could be loaded into the hollow central portion of a structural allograft device such as the fibular ring allograft device shown in FIG. 6, or machined allograft dowels, before insertion of the structural device into the prepared inter-vertebral body space.

The lyophilized putty, no matter what shape, is a firm but pliable medical device that will retain its shape without a containment device as required with putty. Because the device is solid, it is easy to locate or position in-vivo and, in the moist environment of the body, it will hold its shape well and for an extended period of time. Because the lyophilized putty is porous, it adsorbs blood and other beneficial cell containing body fluids, such as bone marrow aspirate, contributing to its superior bone repair efficacy in comparison to the analogous putty. In addition these lyophilized putty devices are easier to terminally steam sterilize than the analogous putty because there is virtually no moisture present to boil and "blow-out" of the containment device (syringe). The glycerin or other fluid material that is present in the formulation lends pliability but has a low vapor pressure.

NaCMC is a key component of the hydrogel utilized in making the lyophilized putty. It is stable to the relatively high pH of the product. NaCMC is stable to steam sterilization and doesn't interfere with the biological action of the product. Other polysaccharide hydrogels such as hydroxyethyl cellulose (HEC), hydroxypropyl methylcellulose (HPC), methylcellulose (MC), and ethylcellulose (EC) may be suitable substitutes for NaCMC. Some hydrogel materials, such as hyaluronic acid and chitosan, are not satisfactory because steam sterilization will cause these materials to degrade, losing viscosity and the ability to suspend particles.

Having described the present invention, it will be understood by those skilled in the art that many changes in construction and widely differing embodiments and applications of the invention will suggest themselves without departing from the scope of the present invention.

What is claimed is:

1. A method for preparing a porous and pliable medical device useful for repairing bone damage and promoting bone formation in mammals, the method comprising the steps of:
   (a) preparing a quantity of a hydrogel material by mixing (i) a quantity of polymer selected from sodium carboxymethylcellulose, hydroxyethyl cellulose, hydroxypropyl methylcellulose, methylcellulose, and ethylcellulose with (ii) a quantity of glycerin, and (iii) a quantity of water;
   (b) mixing said hydrogel material with a quantity of anorganic bone mineral particles coated with P-15 peptide to form a putty; and
   (c) lyophilizing said putty, forming the porous and pliable medical device comprising about 85% (w/w) of said anorganic bone mineral particles coated with P-15 peptide and about 11.5% (w/w) glycerin, wherein prior to step (c) said hydrogel material or said putty is placed under a partial vacuum.

2. The method of claim 1, wherein said polymer is sodium carboxymethylcellulose.

3. The method of claim 2, wherein said porous and pliable medical device comprises about 2.5% (w/w) sodium carboxymethylcellulose.

4. The method of claim 1, wherein said anorganic bone mineral particles have diameters between 50 microns to 2,000 microns.

5. The method of claim 4, wherein said anorganic bone mineral particles have diameters between 250 microns to 425 microns.

6. The method of claim 1, wherein prior to step (c) said hydrogel material is placed under a partial vacuum.

7. The method of claim 1, wherein prior to step (c) said putty is placed under a partial vacuum.

8. The method of claim 1 further comprising the step of sterilizing the pliable medical device.

9. The method of claim 8, wherein said sterilizing comprises the steps of:
   (i) placing the pliable medical device in a container;
   (ii) placing said container containing the pliable medical device into a steam autoclave; and
   (iii) heat sterilizing said porous and pliable medical device in said steam autoclave.

10. The method of claim 1, wherein step (c) further comprises shaping said putty into the form of at least a one of a cylinder, a cube, a sheet, a star, a toroid, a pyramid, a sphere, and an irregular shape prior to lyophilizing said putty.

11. The method of claim 10, wherein said shape is a cylinder.

12. The method of claim 10, wherein said shape is a cube.

13. The method of claim 10, wherein said shape is a sheet.

14. The method of claim 1, further comprising cutting said porous and pliable medical device to reduce the size of said porous and pliable medical device prior to implantation.

15. The method of claim 1, wherein said polymer is hydroxyethyl cellulose.

16. The method of claim 1, wherein said polymer is hydroxypropyl methylcellulose.

17. The method of claim 1, wherein said polymer is ethylcellulose.

* * * * *

UNITED STATES PATENT AND TRADEMARK OFFICE
CERTIFICATE OF CORRECTION

PATENT NO. : 8,048,443 B2
APPLICATION NO. : 11/305715
DATED : November 1, 2011
INVENTOR(S) : James J. Benedict et al.

It is certified that error appears in the above-identified patent and that said Letters Patent is hereby corrected as shown below:

Title page, under OTHER PUBLICATIONS, in Nguyen, Hieu, replace "Communictins" with --Communications--;

Under OTHER PUBLICATIONS, in Schrier, Jay et al., replace "Effect of Freeze-Dried" with --Effect of a Freeze-Dried--;

Under OTHER PUBLICATIONS, in Schrier et al., replace "PharmscTech" with --PharmSciTech--.

Title Page 2, under OTHER PUBLICATIONS, in Patel et al., replace "Patel e al." with --Patel et al.--.

Signed and Sealed this
Fourteenth Day of January, 2014

Michelle K. Lee
*Deputy Director of the United States Patent and Trademark Office*